United States Patent
Dasgupta (10) Patent No.: US 10,180,394 B2
(45) Date of Patent: Jan. 15, 2019

(54) SYSTEMS AND METHODS FOR PERFORMING CAVITY-ENHANCED ABSORPTION SPECTROSCOPY

(71) Applicant: Board of Regents, The University of Texas System, Austin, TX (US)

(72) Inventor: Purnendu Dasgupta, Arlington, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 15/523,642

(22) PCT Filed: Nov. 6, 2015

(86) PCT No.: PCT/US2015/059400
§ 371 (c)(1),
(2) Date: May 1, 2017

(87) PCT Pub. No.: WO2016/073821
PCT Pub. Date: May 12, 2016

(65) Prior Publication Data
US 2017/0315052 A1   Nov. 2, 2017

Related U.S. Application Data

(60) Provisional application No. 62/076,160, filed on Nov. 6, 2014.

(51) Int. Cl.
*G01J 3/00* (2006.01)
*G01N 21/33* (2006.01)
(Continued)

(52) U.S. Cl.
CPC ........... *G01N 21/33* (2013.01); *G01N 21/031* (2013.01); *G01N 21/31* (2013.01); *G01N 33/1846* (2013.01)

(58) Field of Classification Search
CPC .. G01N 21/314; G01N 21/33; G01N 21/3504; G01J 3/10; G01J 3/42
(Continued)

(56) References Cited

U.S. PATENT DOCUMENTS

| | | |
|---|---|---|
| 3,958,941 A | 5/1976 | Regan |
| 4,304,996 A | 12/1981 | Blades |

(Continued)

FOREIGN PATENT DOCUMENTS

| | | |
|---|---|---|
| EP | 0471067 B1 | 2/2003 |
| KR | 100903133 B1 | 6/2009 |

OTHER PUBLICATIONS

International Search Report for PCT/US2015/059400 dated Jan. 22, 2016.
(Continued)

*Primary Examiner* — Md M Rahman
(74) *Attorney, Agent, or Firm* — Thomas | Horstemeyer, LLP (57) ABSTRACT

In one embodiment, a cavity-enhanced absorption spectroscopy system includes a cavity-enhanced absorbance cell in which a liquid sample can be provided for purposes of evaluation, the absorbance cell having diffusely reflective inner surfaces, a light source configured to emit light into the liquid sample within the absorbance cell, and a light detector configured to capture the light after it has passed through the liquid sample.

19 Claims, 8 Drawing Sheets

(51) Int. Cl.
  G01N 21/31 (2006.01)
  G01N 21/03 (2006.01)
  G01N 33/18 (2006.01)
(58) Field of Classification Search
  USPC .......................................................... 356/51
  See application file for complete search history.

(56) References Cited

U.S. PATENT DOCUMENTS

| | | | |
|---|---|---|---|
| 4,802,761 A * | 2/1989 | Bowen | G01N 21/03 |
| | | | 356/246 |
| 5,047,212 A | 9/1991 | Blades | |
| 5,106,754 A | 4/1992 | Steele | |
| 5,132,094 A | 6/1992 | Godec | |
| 5,425,919 A | 6/1995 | Inoue | |
| 5,604,587 A | 2/1997 | Che et al. | |
| 5,781,342 A | 7/1998 | Hannon et al. | |
| 5,902,751 A | 5/1999 | Godec | |
| 5,908,415 A * | 6/1999 | Sinofsky | A61L 2/10 |
| | | | 606/15 |
| 6,015,610 A | 1/2000 | Minor et al. | |
| 6,444,474 B1 | 9/2002 | Thomas | |
| 6,723,565 B2 | 4/2004 | Davenport | |
| 6,839,140 B1 | 1/2005 | OKeefe et al. | |
| 7,154,595 B2 | 12/2006 | Paldus et al. | |
| 8,557,679 B2 | 10/2013 | Chuang et al. | |
| 2012/0205547 A1 | 8/2012 | Klinkhammer | |

OTHER PUBLICATIONS

Bevilacqua, et al., "Ultrapure Water-The standard for resistivity measurements of ultrapure water", 16th Annual Semiconductor Pure Water and Chemical Conference, 1997.
Weidner, et al., "Reflection properties of pressed polytetrafluorethylene powder", J. Opt. Soc. Am., vol. 17 No. 7, Jul. 1981.
Tsai, et al., "Proceedings of SPIE, A comparison of optical properties between solid PTFE (Teflon) and (los density) sintered PTFE", Optical Engineering-FApplications; International Society for Optics and Photonics, 2008.
Silva, et al., "Reflectance of polytetrafluoroethylene for xenon scintillation light", Journal of Applied Physics 107, 2010.
Janecek, Martin, "Reflectivity Spectra for Commonly Used Reflectors", IEEE transaction on nuclear science, vol. 59, No. 3, Jun. 2012.
Nutter, et al., "Sintered Halon as a diffuse reflecting liner for light integration boxes", Nuclear Instruments and Methods in Physics Research Section A: Accelerators, Spectrometers, Detectors and Associated Equipment, Elsevier, vol. 310, Issue 3, Dec. 1991.
Platt, et al., "Simultaneous measurement of atmospheric CH2O, O3, and NO2 by differential optical absorption", Journal of Geophysical Research: Oceans, 84, 1978.
Lei, Wei., et al., "Determination of Phosphorus in Natural Waters by Long-Capillary-Cell Absorption Spectrometry", Anal. Chem, 55, 1983.
Fuwa, et al., "Colorimetry with a total-reflection long capillary cell", Analytical Chemistry, 56, 1984.
Fujiwara, et al., "Liquid Core optical fiber total reflection cell as a colorimetric detector for flow injection analysis", Analytical Chemistry, 57, 1985.
Torchio, et al., "High-reflectivity Hfo2/Sio2 ultraviolet mirrors", Applied Optics, 41, 2002.
Sneppen, et a., "Cavity ring-down spectroscopy for detection in liquid chromatography: extension to tunable sources and ultraviolet wavelengths", Applied spectroscopy, vol. 60, No. 8, 2006.
Fiedler, et al., "Incoherent broad-band cavity-enhanced absorption spectroscopy of liquids", Review of Scientific Instruments 76, 2005.
Hallock, et al., "Directo monitoring of absorption in solution by cavity ring-down spectroscopy", Anal. Chem, 74, 2002.
Kirk, John, "Point-source integrating-cavity absorption meter: theoretical principles and numberical modeling", Applied optics, vol. 36, No. 24, Aug. 1997.

Seetohul, et al., "Broadband cavity enhanced absorption spectroscopy as a detector for HPLC", Anal. Chem, 81, 2009.
Snyder, et al., "Cavity ring-down spectroscopy as a detector for liquid chromatography", Anal. Chem, 75, 2003.
Tsai, et al., "Proceedings of SPIE, A comparison of optical properties between solid PTFE (Teflon) and (los density) sintered PTFE", Optical Engineering+Applications; International Society for Optics and Photonics, 2008.
Van Hall, et al., "An Instrumental Method for Rapid Determination of Carbonate and Total Carbon in Solutions", Analytical Chemistry, 1967.
Huber, et al., "Flow injection analysis of organic and inorganic carbon in the ow-ppb range", Analytical Chemistry, 1991.
Huber, et al., "A new method for the characterization or organic-carbon in aquatic systems", International Journal of Environmental Analytical Chemistry, 1992.
Bender, et al., "Portable Continuous TOC Monitoring in a Semiconductor Water System", Ultrapure Water, 1999.
Emery, et al., "The Total Organic Carbon Analyzer and its Application to Water Research", Journal (Water Pollution Control Federation), 1971.
Dobbs, et al., "The use of ultra-violet absorbance for monitoring the total organic carbon content of water and wastewater", Water Research 1972.
MacCraith, et al., "Results of a cross-comparison study" optical monitoring of total organic carbon (TOC) of a limited range of samples, Sensors and Actuators B Chemical, 1994.
Naffrechoux, et al., "Diode-array ultraviolet detector for continuous monitoring of water quality", Analytica chimica acta, 1992.
ELGA Technology Note; "Monitoring TOC in Ultra-Pure Laboratory Water", Note No. 7; Aug. 2006.
Potter, et al., "Determination of Total Organic Carbon and Specific UV Absorbance at 254 nm in Source Water and Drinking Water," Office of Research and Development, National Exposure Research Laboratory. Feb. 2005.
Bourgeois, et al., "On-line monitoring of wastewater quality: A Review", Journal of Chemical Technology and Biotechnology; 76: 337-348, 2001.
Zaps Technologies; Correlation Report; LiquIDTM E. Coli Correlation Study on Oak Creek; Jun. 2012.
Dresser, Edwards, "Relationships between ultraviolet absorbance and total organic carbon in two upland catchments", Water Research, Elsevier, vol. 21, Issue 1, Jan. 1987.
Power, et al., "Optical Absorbance of Dissolved Organic Matter in Natural Water Studies Using the Thermal Lens Effect", Analytica chimica acta 1992.
Pages, et al., "Dissolved organic matter and UV absorption in a tropical hyperhaline estuary", Elsevier, Science of the Total Environment, vol. 99, Issues 1-2, Dec. 1990.
Ferrari, et al., "Relationiship between the optical properties of chromophoric dissolved organic matter and total concentration of dissolved organic carbon in the southern Baltic Sea region", Elsevier, Marine Chemistry 55, 1996.
Sheppard, C., "Problems with the use of ultra-violet absorption for measuring carbon compounds in a river system", Elsevier, Water Research, vol. 11, Issue 11, 1977.
Ferrari, Giovanni, "The relationship between chromophoric dissolved organic matter and dissolved organic carbon in the European Atlantic coastal area and in the West Mediterranean Sea", Elsevier, Marine Chemistry 70, 2000.
Weishaar, et al, "Evaluation of specific ultraviolet absorbance as an indicator of the chemical composition and reactivity of dissolved organic carbon", Environ. Sci. Technol. 37, 2003.
White, John, "Long Optical Paths of Large Aperture", J. Opt. Soc. Am, 1942.
Herriott, et al., "Folded Optical Delay Lines", Applied Optics, Vo. 4, 1965.
Dasgupta, Pumendu, "Multipath cells for extending dynamic range of optical absorbance measurements", Anal. Chem, 56, 1984.
Dasgupta, et al., "Optical Cells with Partially Reflecting Windows as Nonlinear Absorbance Amplifiers", Analytical Chemistry, 59, 1987.

(56) References Cited

OTHER PUBLICATIONS

O'Keefe, Anthony, "Integrated cavity output analysis of ultra-weak absorption", Chemical Physics Letters 293, Sep. 4, 1998.

O'Keefe, et al., "Cavity ringdown optical spectrometer for absorption measurements using pulsed laser sources", AIP Review of Scientific Instruments, 59, 1988.

O'Keefe, et al. "Integrated cavity output spectroscopy", Elsevier, Chemical Physics Letters, Jul. 9, 1999.

Kiwanuka, et al., "Senstive method for the kinetic measurement of trace species in liquids using cavity enhanced absorption spectroscopy with broad bandwidth supercontinuum radition", Anal. Chem, 82, 2010.

Seetohul, et al., "Liquid-phase broadband cavity enhanced absorption spectroscopy (BBCEAS) studies in a 20 cm cell", Analyst, 134, 2009.

Neil, et al., "Broadband cavity-enhanced absorption spectroscopy for real time, in situ spectral analysis of microfluidic droplets," Lab on a Chip, 2011.

van der Sneppen, et al., "Following interfacial kinetics in real time using broadband evanescent wave cavity-enhanced absorption spectroscopy: a comparsion of light-emitting diodes and supercontinuum sources", Analyst, 135, 2010.

Dasgupta, et al., "Cavity-Enhanced Absorption measurements across broad absorbance and reflectivity ranges", Analytical Chemistry, 2014.

Fry, et al., "Integrating cavity absorption meter", Applied Optics, 1992.

International Technology Roadmap for Semiconductors, 2009 Edition, Yield Enhancement.

Semiconductor Equipment and Materials International; Guide for Ultrapura Water Using Semiconductor Processing; 2011.

The United States Pharmacopeia 35, The National Formulary 30, vol. 1, 2012.

European Pharmacopeia 5.0; 22.44 Total Organic Carbon in Water for Pharmaceutical Use, 2005.

Bader, et al., "Online total organic carbon (TOC) as a process analytical technology for cleaning validation risk management", Pharmaceutical Engineering, 2009.

Baffi, et al., "A total organic carbon analysis method for validating cleaning between products in biopharmaceutical manufacturing", J. Parenter Sci Technol. 1991.

Clifford, R.H., Supporting pharmaceutical cleaning validation with TOC and UV-VIS spectrophotometric analysis, Amerian Laboratory, 42, 2010.

Strege, et al., "Total organic carbon analysis of swab samples for the cleaning validation of bioprocess fermentation equipment", BioPharm International, 9, 1996.

Wallace, et al., "Implementing total organic carbon analysis for cleaning validation", Pharmaceutical Technology, 2004.

United States Food and Drug Administration, Validation of Cleaning Processes, Jul. 1993.

Bevilacqua, A., et al., "Updating international standards for pharmaceutical waters", The Pharmaceutical Solutions Update, Mar. 2008.

DeGenova, John, "Evaluation of 3 commerically available, on-line TOC analyzers for monitoring recycled water in semiconductor processing", Ultrapure Water Journal, Nov. 1998.

Matthews, R.W., et al., "Photocatalytic oxidation for total organic carbon analysis", Analytica Chimica Acta, 233, 1990.

Izumi, et al., "Heterogeneous photocatalytic oxidation of hydrocarbons on platinized titanium dioxide powders", The Journal of Physical Chemistry, 84, 1980.

Godec, Richard, "The performance comparison of ultrapure water TOC analyzers using an automated standard addition apparatus", Semiconductor Pure Water and Chemicals Conference, 2000.

Peyton, Gary, "The free-radical chemistry of persulfate-based total organic carbon analyzers", Marine Chemistry, 41, 1993.

Rydzewski, et al., "Undetectable TOC in UPW can influence DUV photolithography processes", Proceedings of the smiconductor pure water and chemicals conference, 2002.

Godec, Richard, "Measurement and removal of trace levels of urea in semiconductor high-purity water", Ultrapure water Europe, 2002.

\* cited by examiner

SYSTEMS AND METHODS FOR PERFORMING CAVITY-ENHANCED ABSORPTION SPECTROSCOPY

CROSS-REFERENCE TO RELATED APPLICATION

This application is the 35 U.S.C. § 371 national stage application of PCT Application No. PCT/US2015/059400, filed Nov. 6, 2015, where the PCT claims priority to U.S. Provisional Application Ser. No. 62/076,160, filed Nov. 6, 2014, both of which are herein incorporated by reference in their entireties.

NOTICE OF GOVERNMENT-SPONSORED RESEARCH

This invention was made with Government support under grant/contract number CHE-1246368, awarded by the National Science Foundation. The Government has certain rights in the invention.

BACKGROUND

Total organic carbon (TOC) analysis is one of the most critical tests performed in high purity water systems used in the pharmaceutical and semiconductor industries. TOC is a measure of the total carbon present excluding all inorganic carbon in the form $CO_2$, $HCO_3^-$, or $CO_3^{2-}$. Stringent sub µg/L restrictions have been set for ultra-pure water (UPW) by the International Technology Roadmap for Semiconductors (ITRS) and the Semiconductor Equipment and Materials International (SEMI) due to the deleterious effect of even trace organics on production. Additionally, SEMI F63 stipulates that any TOC analyzer should have a limit of detection of 50 ng/L or less. Pharmaceutical TOC, however, is less critical, requiring water for injection to be less than 500 µg/L carbon according the United States and European Pharmacopeias, and any method used for TOC must not have a limit of detection above 50 µg/L carbon.

Because TOC is a measure of all organic compounds present, no single technique is adequate to measure the compounds directly due to the range of chemistries present. For this reason, nearly all TOC analyzers are dependent upon the indirect measurement of carbon species following oxidation of the organics and measurement as $CO_2$. The two primary methods of determination of the produced $CO_2$ are non-dispersive infrared absorption spectroscopy (NDIR) and conductivity. While these methods are generally effective, each requires digestion of the sample prior to analysis.

Absorption spectroscopy offers an alternative that does not require digestion prior to analysis. In the deep ultraviolet (UV) light, all compounds absorb to some degree. Further, in general, absorption by an overwhelming majority of compounds increases monotonically at wavelengths below 220 nm and hence the sensitivity increases with decreasing wavelength. The smaller the probe wavelength, the smaller the particles that can be detected by scattering. Absorption methods have previously been used to measure TOC in a variety of matrices such as waste waters, natural, fresh, and sea waters, and purified water streams. Unfortunately, current commercially available equipment has a low operating limit of 0.1 mg/L, which does not even meet the mandated limit of detection (LOD) for pharmaceutical waters, much less the LOD of the semiconductor industry.

The LOD of absorption spectroscopy can be increased by increasing the path length of the absorbance cell to increase its sensitivity. Cavity-enhanced techniques can be used to increase the effective path length thereby lowering the limit of detection without requiring larger physical paths. In cavity-enhanced absorption spectroscopy (CEAS), the absorbance cell has reflective surfaces so that light bounces back and forth across the same path multiple times before detection. To date, CEAS has primarily been applied to samples in the gas phase and has shown only limited promise for use on liquids.

In view of the above discussion, it can be appreciated that it would be desirable to have an effective system and method for performing cavity enhanced absorption spectroscopy on liquids.

BRIEF DESCRIPTION OF THE DRAWINGS

The present disclosure may be better understood with reference to the following figures. Matching reference numerals designate corresponding parts throughout the figures, which are not necessarily drawn to scale.

DETAILED DESCRIPTION

As described above, it would be desirable to have an effective system and method for performing cavity-enhanced absorption spectroscopy (CEAS) on liquid samples. Disclosed herein are examples of such systems and methods. In some embodiments, a CEAS system comprises a cavity-enhanced absorbance cell in which a liquid sample can be provided for purposes of evaluation. Unlike conventional CEAS cells that use mirrors through which light is launched, the entire absorbance cell behaves as a reflecting cavity and a diffuse reflector. In some embodiments, the absorbance cell can be made of a fluorocarbon-based material, such as polytetrafluoroethylene (PTFE), which exhibits high diffuse reflectivity across a large wavelength range. In cases in which PTFE or another hydrophobic material is used, the inner surfaces of the cell can be treated so as to render them hydrophilic to prevent the formation of bubbles that can cause scattering and generate noise. The evaluation of the liquid can, for example, comprise determining the total organic carbon (TOC) in the liquid or detecting the presence of any substance (including particles) present in the liquid that absorbs or scatters light. In either case, light from a light source is directed into the cell and, after it passes through the liquid, is detected by a light detector. The light detector can comprise a spectrometer that can separate and detect different source wavelengths. An advantage of a spectrometric detector is that a long wavelength with which there is unlikely to be absorption (or at least the absorption will be low) can be used as a reference to compensate for any drift in the light intensity. The spectrometer readings can then be analyzed to identify the components contained within the liquid.

In the following disclosure, various specific embodiments are described. It is to be understood that those embodiments are example implementations of the disclosed inventions and that alternative embodiments are possible. All such embodiments are intended to fall within the scope of this disclosure.

Figure 1:
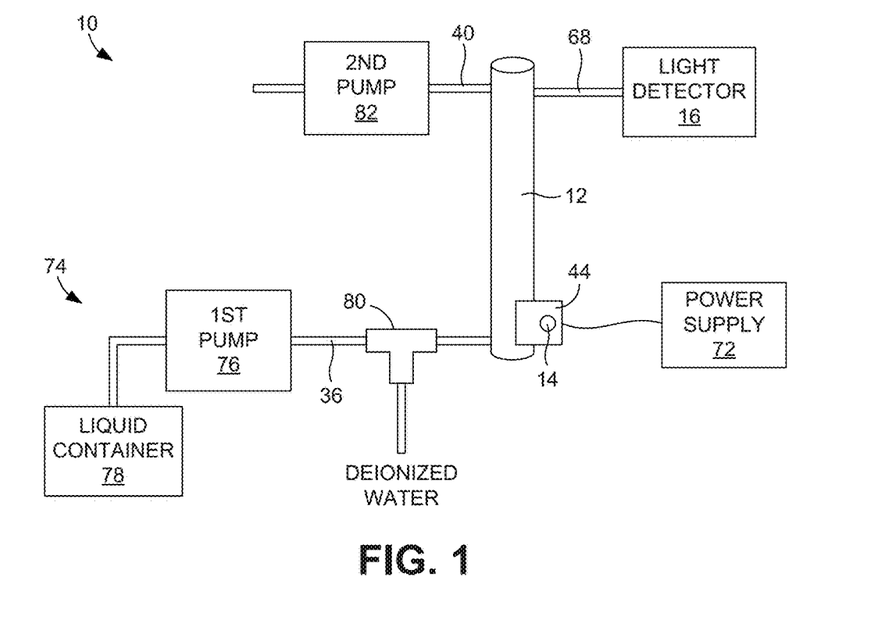
FIG. 1 is a schematic diagram of an embodiment of a cavity-enhanced absorption spectroscopy (CEAS) system.

FIG. 1 illustrates an example embodiment of a CEAS system 10 that can be used to evaluate liquid samples. As shown in the figure, the system 10 generally comprises a cavity-enhanced absorbance cell 12 into which the liquid sample can be delivered, a light source 14 that emits light into the cell, and a light detector 16 that captures the light after it has passed through the liquid sample.

Figure 2:
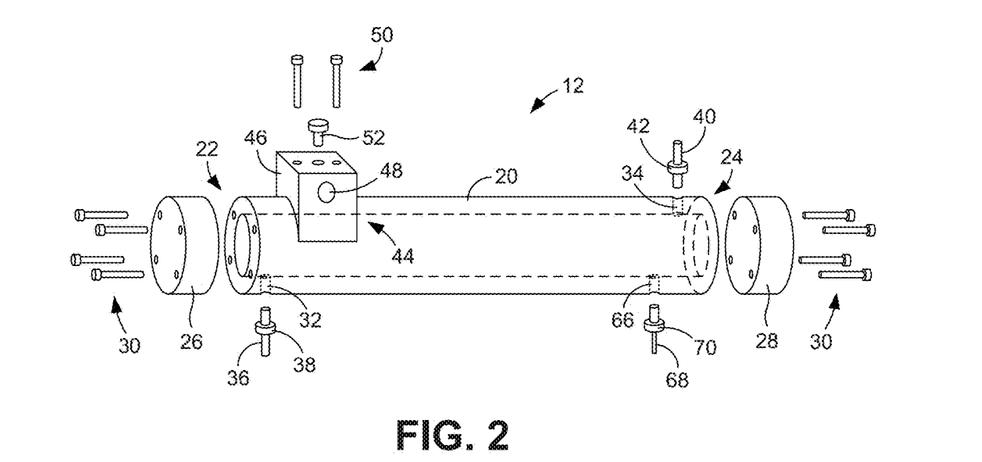
FIG. 2 is schematic perspective view of an embodiment of a cavity-enhanced absorption cell of the system of FIG. 1.

FIG. 2 illustrates an example construction for the cavity-enhanced absorbance cell 12 shown in FIG. 1. In this example, the cell 12 comprises an elongated hollow cylindrical tube 20 having opposed first and second ends 22 and 24 to which are respectively mounted end caps 26 and 28. As indicated in FIG. 2, the end caps 26, 28 can be secured to the ends 22, 24 of the tube 20 with threaded fasteners 30, such as screws, that pass through fastener openings formed in the end caps and the tube. By way of example, the tube 20 can have an inner diameter of approximately 0.01 to 50 cm, a length of approximately 1 to 200 cm, and a wall thickness of approximately 1 to 40 mm.

Both the tube 20 and the end caps 26, 28 are made of a material that exhibits diffuse reflectance for the wavelengths emitted by the light source 14. As is known in the art, "diffuse reflection" is the reflection of light from a surface such that an incident ray is reflected at many angles rather than at just one angle, as in the case of specular reflection. In some embodiments, the tube 20 and end caps 26, 28 are made of a fluorocarbon-based material, such as a fluoropolymer like PTFE. PTFE is a diffuse reflector that maintains high reflectivities even into the "deep" ultraviolet (UV) (i.e., 254 nm and below). In some embodiments, the inner surfaces (i.e., reflective surfaces) of each of the tube 20 and the end caps 26, 28 are treated to make them hydrophilic. By way of example, the inner surfaces can be oxygen plasma treated to achieve this result. In some embodiments, the depth of the treated material is less than the wavelength of the light that is introduced into the cell 12.

With further reference to FIG. 2, the tube 20 includes a liquid inlet port 32 at its first end 22 and a liquid outlet port 34 at its second end 24 that enable liquid, such as water, to be delivered into and be removed from the absorbance cell 12. This liquid can flow to inlet port 32 through an inlet line 36 that connects to the tube 20 with a coupler 38, and can flow from the outlet port 34 through an outlet line 40 that connects to the tube with a coupler 42.

As shown in FIG. 1, the light source 14 can be mounted to the absorbance cell 12 with a light housing 44. FIG. 2 shows an example embodiment for this housing 44. As illustrated in FIG. 2, the housing 44 can comprise a body 46 that is formed from a block of metal, such as aluminum. Formed in the body 46 is a passage 48 into which the light source 14 can be passed. The body 46 can be secured to the tube 20 of the cell 12 with threaded fasteners 50, such as screws. In addition, the housing 44 can include a set screw 52 that is used to secure the light source 14 when it is provided within the housing 44.

Figure 3:
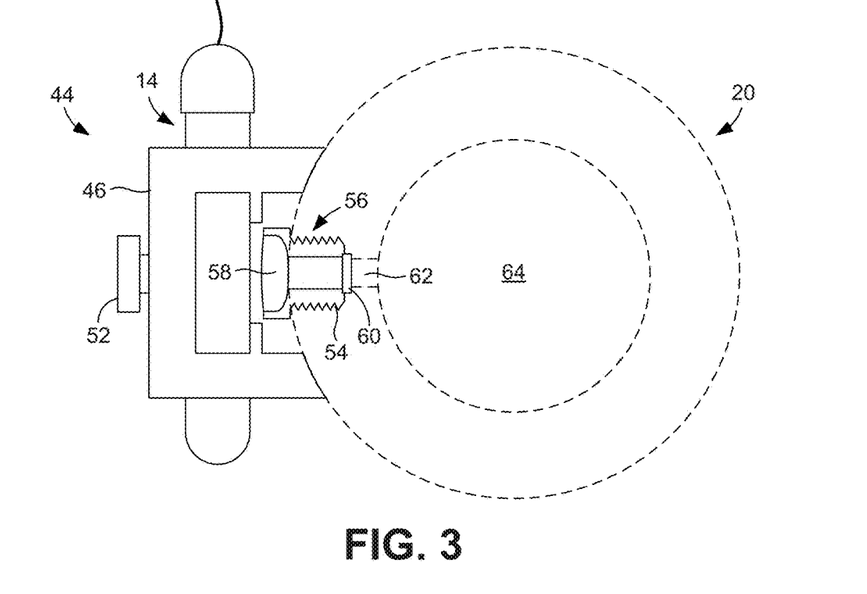
FIG. 3 is a schematic cross-section of an embodiment of a light source housing of the system of FIG. 1.

Further details for the illustrated housing embodiment are shown in FIG. 3. As indicated in this figure, the housing 44 overlies a threaded opening 54 that is formed in the wall of the tube 20. A hollow, threaded lens holder 56 is threaded into the opening 54 and supports at one of its ends a lens 58. In some embodiments, the lens 58 comprises a plano-convex fused silica lens. At the other end of the lens holder 56 is a light window 60 through which light focused by the lens 58 can pass. In some embodiments, the window 60 comprises a fused silica window. A small entrance aperture 62 is formed in the wall of the tube 20 adjacent the window 60 so that light that passes through the window can further enter the inner space 64 of the tube and, therefore, the cell 12. In some embodiments, the aperture 62 is approximately 1 to 50 mm in diameter. By way of example, the light source 14 can comprise a cylindrical zinc pen-ray lamp that emits multiple lines of UV light.

With reference back to FIG. 2, light emitted into the tube 20 by the light source 14 can escape the tube through an exit aperture 66 provided at the second end 24 of the tube. This light can travel through an optical fiber 68 that connects to the tube 20 with a coupler 70 to the light detector 16 (see FIG. 1). By way of example, the light detector 16 can comprise a charge-coupled (CCD) spectrometer, a photodiode array spectrometer, or a photomultiplier tube array spectrometer. In some embodiments, the intensity of the 214 nm zinc emission line emitted by the light source 14 can be monitored at the opposite end of the cell 12 to determine absorption or scattering losses.

Referring back to FIG. 1, the system 10 further comprises a power supply 72 that provides power to the light source 14. In addition, the system 10 comprises a sample delivery system 74 that can be used to deliver liquid samples to the absorbance cell 12. In the illustrated embodiment, the sample delivery system 74 includes a first pump 76, such as a syringe pump, that injects a first liquid contained in a liquid container 78 into the inlet line 36. As shown in FIG. 1, a tee fitting 80 can be connected to the inlet line 36 to enable a second liquid to be mixed with the first liquid before it enters the cell 12. By way of example, the first liquid can be water that contains a component to be detected (e.g., organic carbon or particulate matter) and the second liquid can comprise purified water, such as deionized (DI) water.

Also shown in FIG. 1 is a second pump 82, such as a peristaltic pump, that is connected to the outlet line 40. The pump 82 can draw liquid from the absorbance cell 12. During operation of the system 10, the liquid can be continually aspirated by the pump 82.

During use of the system 10, at least the first liquid contained in the liquid container 78 is pumped into the interior space 64 of the absorbance cell 12 using the first pump 76. Once the absorbance cell 12 is filled with liquid, the light source 14 can be activated with power from the power supply 72 to emit light into the liquid. This light will pass through the liquid and reflect off of the inner surfaces of the absorbance cell 12 and will ultimately be received by the light detector 16 via the optical fiber 68. If desired, the liquid in the absorbance cell 12 can be pumped from the cell using the second pump 82 and fresh liquid can be supplied to the cell using the first pump 76 on a continual or continuous basis.

Figure 4:
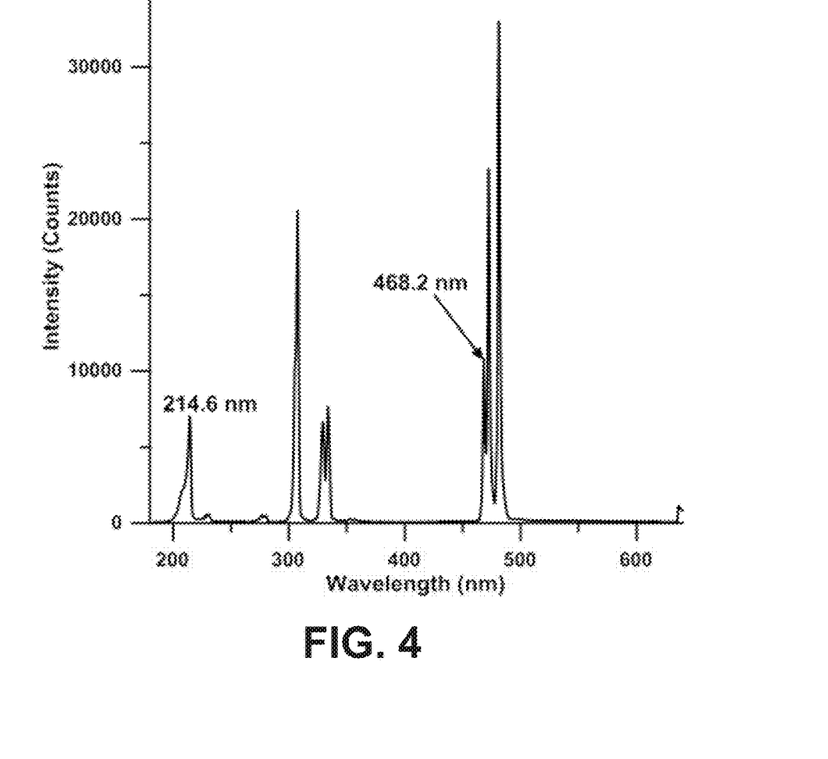
FIG. 4 is a plot of zinc lamp emission spectra measured through an absorption cell using a spectrometer.

A system similar to that described above was constructed for water testing purposes. A sample solution was continually aspirated through the absorbance cell by a Rainin Dynamax peristaltic pump at a flow rate of 6.7 mL/min. A polyether ether ketone (PEEK) tee fitting (www.upchurch.com) positioned upstream from the entrance to the cell allowed a DI water stream (Milli-Q (www.millipore.com) >18.2 MO/cm resistivity and <1 ppb TOC) to be mixed with an organic carbon standard injected using a Kloehn Versa 6 syringe pump. A zinc pen-ray lamp (www.uvp.com) mounted directly to the absorbance cell was used as the light source (powered using a Isodyne ISO-28V 2-8 watt ballast adjustable power supply) and an Avantes 1024×58 array thermoelectric cooled (TEC) CCD spectrometer equipped with a 1000 lines/mm grating blazed at 250 nm and a 50 µm slit (wavelength range 200-660 nm) was used as the detector (www.Avantes.com). Light signals were delivered to the spectrometer with a 1 mm high —OH silica optical fiber (www.polymicro.com). The integration time was set to 2.0 seconds. The 214 nm zinc emission line was monitored for absorbance and the 468.2 nm line was used as a reference line to correct for any lamp drift. The emission spectrum, as was measured by the Avantes spectrometer through the absorbance cell, is shown in FIG. 4.

The absorbance cell was made from a R-11 resin-extruded PTFE pipe (length 12 in., I.D. ⅝ in., O.D. 1½ in.) with two PTFE end caps (1.5 in, diameter, 0.5 in. thick). The PTFE pipe and caps underwent a 30 minute plasma surface treatment by PVA TePla America to make the surface more hydrophilic. The contact angle measured on the treated PTFE was 15° compared to greater than 120° for the untreated PTFE.

A lamp housing was constructed for the zinc lamp out of aluminum. A large PTFE nut was made to contain a pocket for a plano-convex fused silica lens (20 mm diameter, 30 mm focal length, www.edmundoptics.com). The lamp housing pressed against the plano-convex lens holding it in place. The nut inner diameter was 8.6 mm. A corresponding thread was formed in the pipe wall and terminated approximately 2 mm from the interior channel of the tube. A 9 mm hole was drilled through to the interior channel to enable light to enter the channel. The nut was used to hold a fused silica window (10 mm diameter, www.edmundoptics.com) in place and form a seal against the PTFE. The aluminum block was machined to fit snugly against the PTFE pipe. A hole was made through the entire length of the block to receive the zinc lamp. A PTFE sheet was placed behind the lamp to reflect additional UV light into the cell. The lamp was held in place using a nylon screw to provide tension.

A window was cut into the aluminum between the fused silica lens and the zinc lamp. The window was 10 mm wide and 25 mm long. The length dimension ran parallel to the length of the lamp. The shorter dimension enabled the aluminum block to press against the lens and retain it in place. Inlet and outlet ports were drilled into the wall of the pipe approximately 1 cm from the end caps to allow the use of standard ¼-28 PEEK fittings. Opposite the outlet port, and 5 mm nearer to the lamp, a 1.3 mm hole was drilled to fit the 1 mm core silica optical fiber so that the fiber can be in contact with the liquid and flush with the wall. The fiber was held in place using a ¼-28 nut and ferrule. The measured volume of the cell was 54.4 mL.

Figure 5:
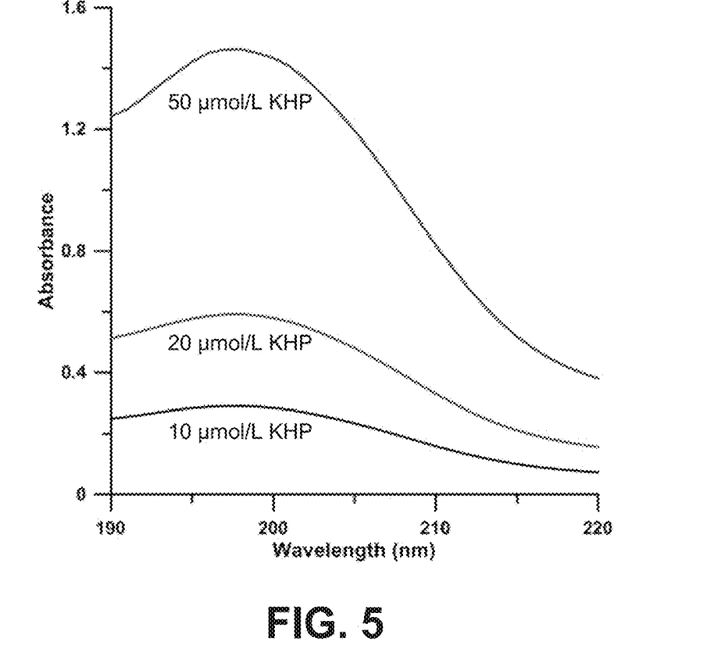
FIG. 5 is a plot of the potassium hydrogen phthalate (KHP) absorption spectrum.
Figure 6:
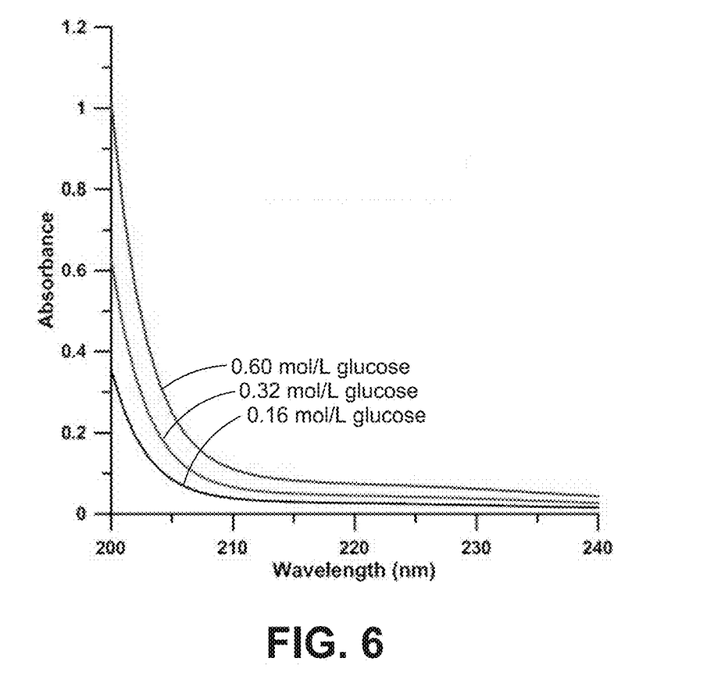
FIG. 6 is a plot of the glucose absorption spectrum.
Figure 7:
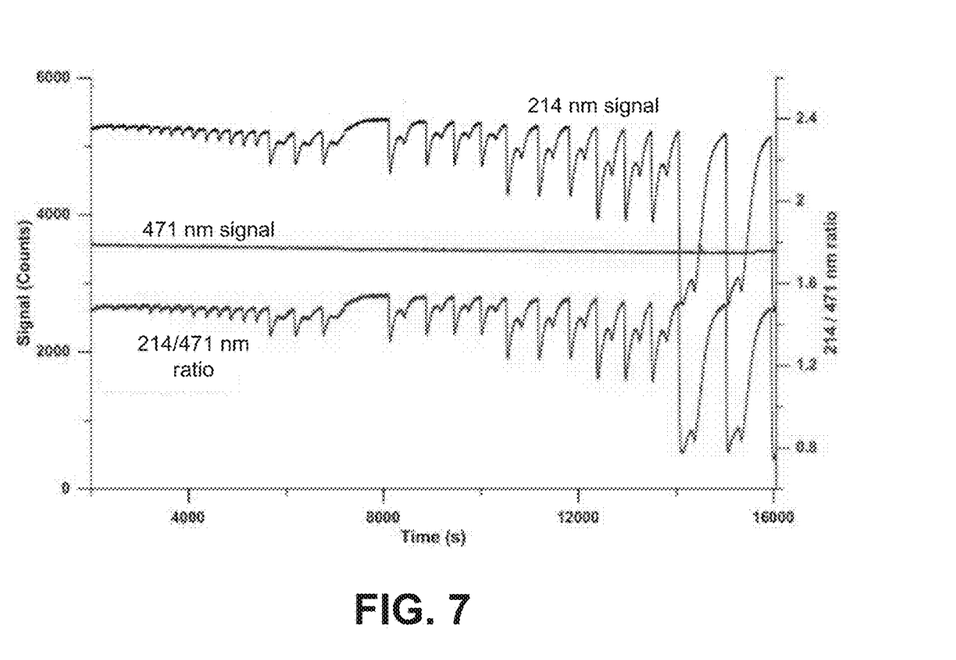
FIG. 7 is a graph that plots 214 nm and 471 nm signals produced as KHP was injected into an absorption cell. The trace produced when the 214 nm is referenced against the 471 nm signal is also included.
Figure 8:
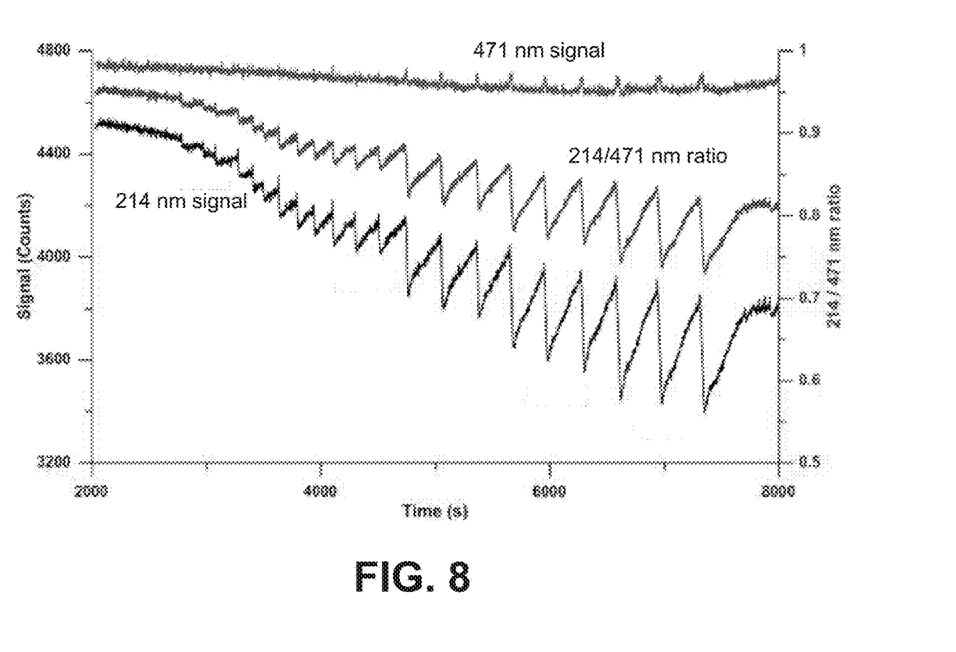
FIG. 8 is a graph that plots 214 nm and 471 nm signals produced as glucose was injected into an absorption cell. The trace produced when the 214 nm is referenced against the 471 nm signal is also included.

Potassium acid phthalate (KHP, >999.95% purity, Mallinckrodt) and glucose (analytical reagent, Mallinckrodt) were used as total organic carbon standards for assessing the device. Solutions of KHP and glucose were prepared in Milli-Q water and the absorption spectra were recorded using a Hewlett Packard 8453 spectrophotometer to obtain molar absorptivities at 214 nm (see FIGS. 5 and 6). The standards were then loaded into the syringe pump to be injected into the absorption cell. Aliquots of standard were injected at 18 mL/min into the flowing DI water stream, ranging in volume from 0.25 mL to 10 for 5 and 50 µM solutions of KHP and 50 mM solutions of glucose. The tubing leading back to the DI water source was of sufficient volume such that no cross-contamination occurred even though the syringe injection rate was faster than the aspiration rate of the peristaltic pump. Raw data for injections of KHP and glucose injections are shown in FIGS. 7 and 8 respectively. The concentrations were calculated based on dilution of the initial injected aliquot into the 54.4 mL cell. Measured values ranged from 2.3 to 644 nM KHP (0.22-62 µg/L carbon) and 0.23 to 9.2 mM glucose (16 to 662 mg/L carbon). The cell was also filled with prepared standards of KHP and the absorbance was measured under static and flowing conditions.

Figure 9:
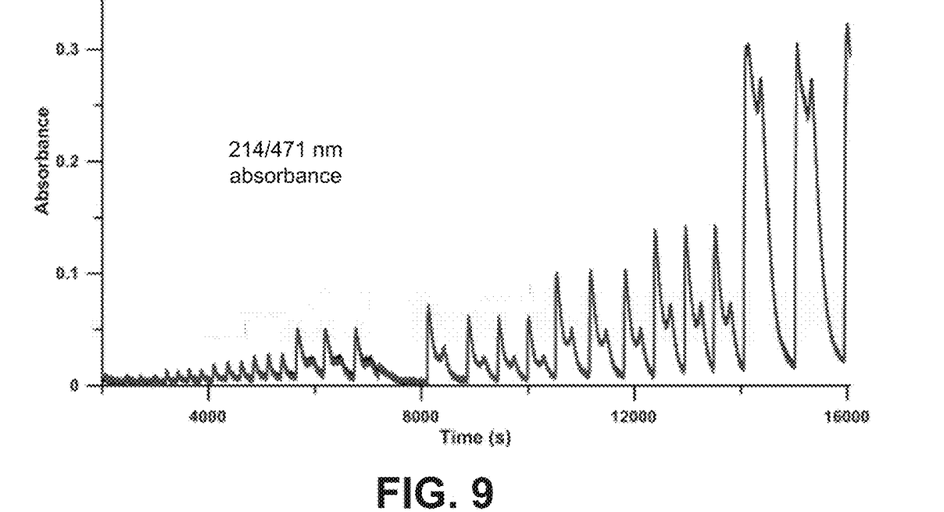
FIG. 9 is a plot of an absorbance signal produced as KHP was injected into the absorption cell. Both the 214 nm line alone and the ratio of the 214 nm line to the 471 nm reference line are plotted.
Figure 10:
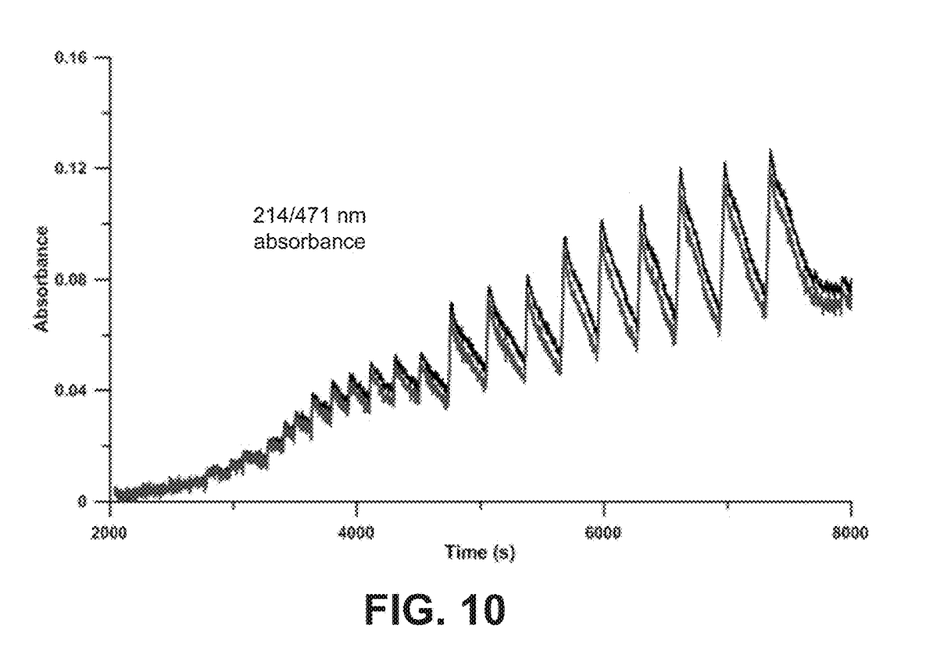
FIG. 10 is a plot of an absorbance signal produced as glucose was injected into the absorption cell. Both the 214 nm line alone and the ratio of the 214 nm line to the 471 nm reference line are plotted.
Figure 11:
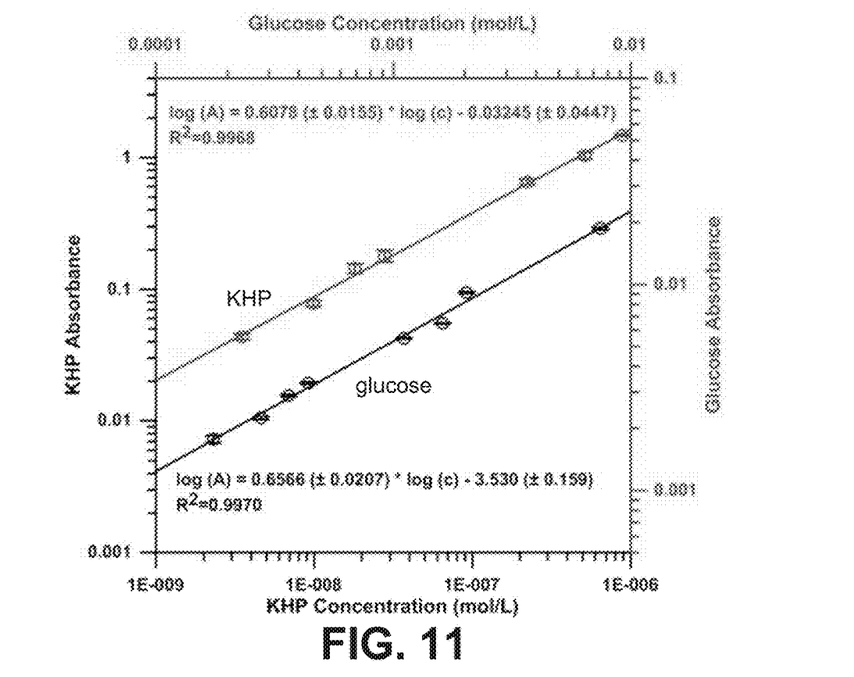
FIG. 11 is a plot of the peak absorbance of injected KHP and glucose versus the concentration injected.

The measured molar absorptivities at 214 nm for KHP and glucose were 11282 and 0.1243 L mol$^{-1}$ cm$^{-1}$, respectively. As mentioned above, aliquots of the standard solutions were injected using the syringe pump into the flowing stream of DI water (the data is presented in absorbance units in FIGS. 9 and 10). The absorbance was calculated using the peak height from the nearest preceding valley. Plots of log concentration vs. log absorbance are shown in FIG. 11. In conventional absorbance spectroscopy in which Beer's law is followed, plots of log concentration vs. log absorbance will yield a slope of 1 since absorbance is a linear function of concentration. Here, slopes of 0.6566±0.0207 and 0.6079±0.0155 were obtained for KHP and glucose, respectively.

Figure 12:
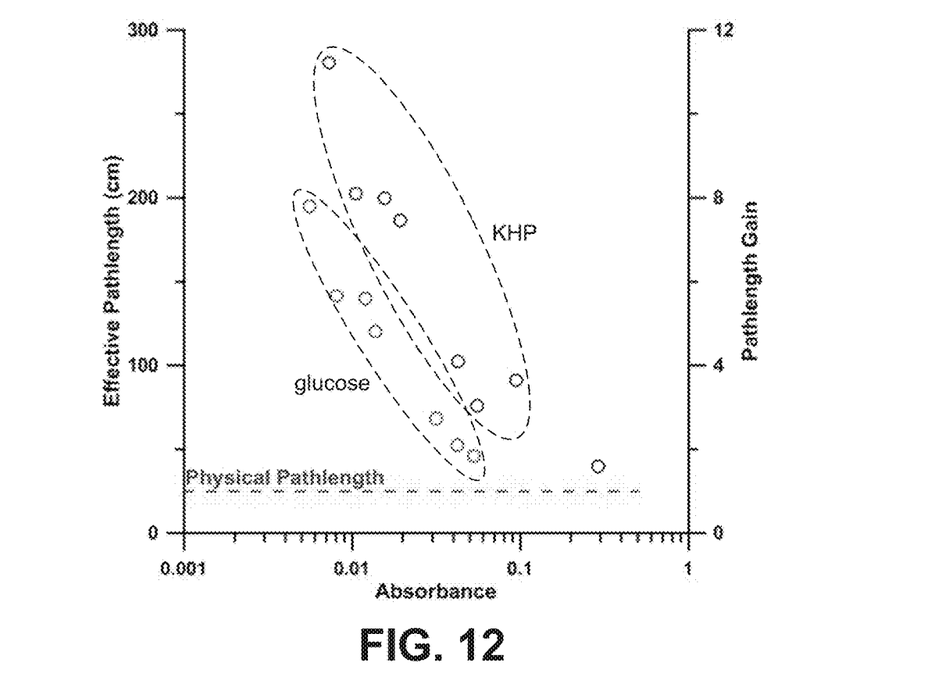
FIG. 12 is a plot of the effective path length of the cavity enhanced absorption cell as a function of absorbance. The path length was determined using the molar absorptivities of KHP and glucose. The gain was calculated as the ratio of the effective to the physical path length of 25 cm.
Figure 13:
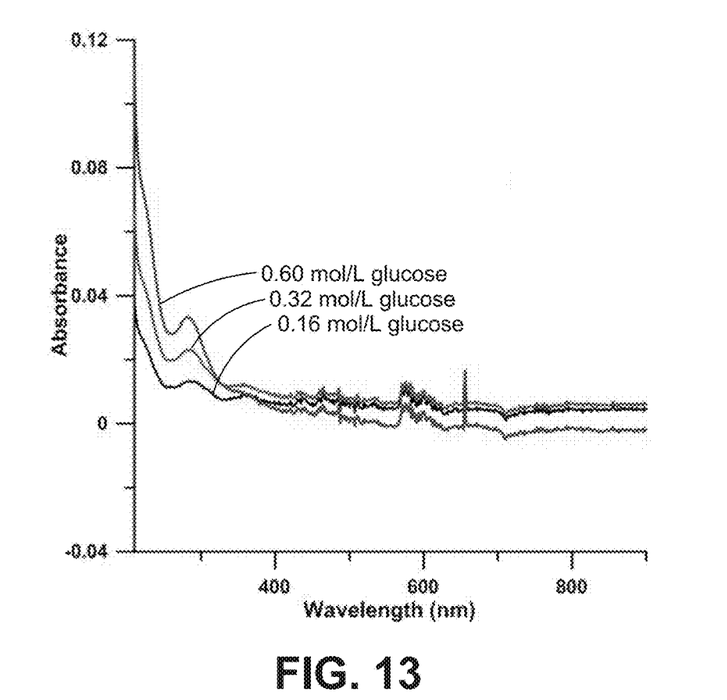
FIG. 13 is a graph that plots the absorbance of glucose from 200 to 900 nm.

The center of the zinc lamp entrance aperture and fiber optic were separated by a length 25 cm and a width of 1.5 cm. The total physical path length was approximately 25 cm, which represents a minimum distance light must traverse before reaching the detector. A physical path of 25 cm was therefore used as a reference. FIG. 12 shows the effective path length as a function of absorbance. The effective path length was calculated using the known absorbance value, the concentration injected, and the molar absorptivity of the compound. The gain over the physical path of 25 cm was also shown. The largest effective path length observed was 280 cm, representing more than an 11 fold increase over the physical path length. Regardless of the compound, the path length dependence on absorbance should remain the same. However, glucose produced consistently lower results. This can be attributed to the difficulty in ascertaining the glucose molar absorptivity at 214 nm. Glucose is very weakly absorbing, almost five orders of magnitude less than KHP. Large amounts were necessary to obtain an absorbance reading at 214 nm. Changes in refractive index become considerable at the levels used. The longer path employed here may help reduce the relative contribution of refractive index effects. Evidence of refractive index effects may be seen in the absorption spectrum of FIG. 13: positive absorbance can be seen up to almost 400 nm above which negative absorbance becomes apparent. Because of the wavelength dependence upon refractive index, a correction using another wavelength is difficult. It is intuitive, however, that, because all absorbance concentrations below 400 nm are positive, refractive index contributions at 214 nm are also positive. This leads to the conclusion that the measured molar absorptivity at 214 nm is likely an overestimation of the true molar absorptivity, resulting in lower calculated effective path lengths. Inspection of the raw data for glucose injections shows that disturbances in the reference baseline are seen at the point of injection. The concentrated sample upon entering the cell passes the lamp increasing transmittance briefly into the cell. No corresponding increase or decrease is seen at the other end after the sample has been thoroughly mixed. It is also interesting to note that this blip does not correspond with a maximum in absorption either but precedes it.

Figure 14:
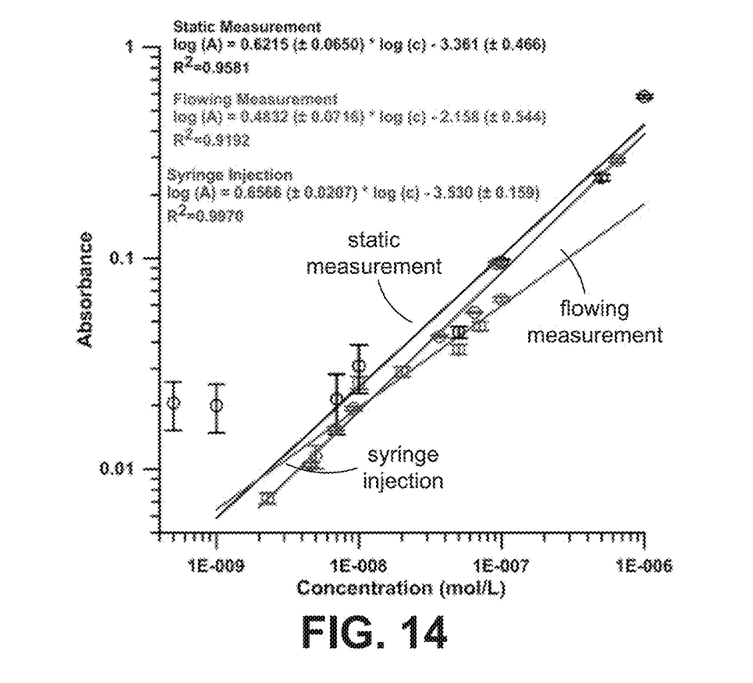
FIG. 14 is a graph that plots the peak absorbance of KHP at given concentrations by three different introduction methods: continuously flowing a fixed concentration, measurement without flow (static), and injecting a concentrated slug into a flowing stream of water.
Figure 15:
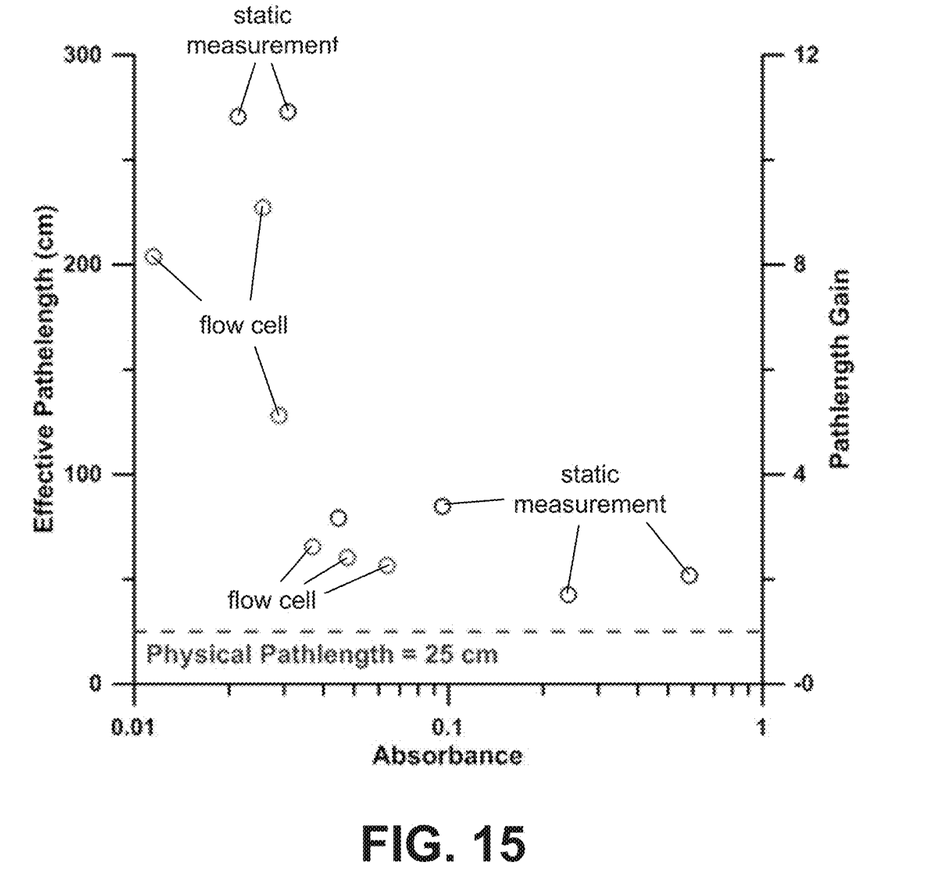
FIG. 15 plot of the effective path length of the cavity-enhanced absorption cell as a function of absorbance for KHP measured upon introduction of a fixed concentration that was both flowing and static. The path length is determined using the molar absorptivity of KHP. The path length gain is calculated as the ratio of the effective to physical path length of 25 cm.

The absorbance cell acts as an integrator. Therefore, complete mixing is not required for accurate absorbance measurements, nor does the cell need to be filled with homogenous solution. The total amount of absorbing species in the cell will have the same absorbance regardless of its location. It was assumed that, because the sample cell is significantly larger than the amount injected, all of the standard will reside within the cell at the peak height before being washed out. This was confirmed by filling the cell with prepared KHP solutions and measuring the absorbance. This was performed under both flowing and static conditions in two separate experiments (see FIG. 14). Results are comparable with the injected mode, but both the flowing and static modes were less reproducible and gave poorer correlation coefficients ($r^2$=0.9581, 0.9192, and 0.9970 for static, flowing, and injected measurements), In addition, for the static measurements, the limit of detection was worse. Anything below 10 nM was statistically indistinguishable, although it still produced a noticeable absorbance compared to the blank. This is likely due to the ease of contamination at such low levels. Similar path length gains (see FIG. 15) were observed with the static measurements, achieving an effective path length of up to 270 cm compared to 280 cm achieved using syringe injection.

Injection of blank solutions showed no change in the baseline, so the limits of detection (LODs) were calculated based on three times the standard deviation of the baseline signal for both KHP and glucose. The LODs for KHP and glucose were 0.484 nM and 64 µM. This corresponds to a carbon concentration of 46.5 ng/L and 4.6 mg/L, respectively. These may be considered likely upper and lower limits of sensitivity. Real TOC measurements will likely reside somewhere in between.

The invention claimed is:

1. A cavity-enhanced absorption spectroscopy system comprising:
    a cavity-enhanced absorbance cell made of a fluorocarbon-based material, the absorbance cell being configured to contain a liquid sample for purposes of evaluation, the absorbance cell having diffusely reflective inner surfaces configured to confine light and reflect the light back and forth through multiple passes such that the absorbance cell functions as an optical cavity having no mirrors;
    a light source configured to emit light into the liquid sample within the absorbance cell; and
    a light detector configured to capture the light after it has passed through the liquid sample.

2. The system of claim 1, wherein the absorbance cell comprises an elongated cylindrical tube.

3. The system of claim 1, wherein the absorbance cell is made of a fluoropolymer.

4. The system of claim 1, wherein the absorbance cell is made of polytetrafluoroethylene (PTFE).

5. The system of claim 1, wherein the material of the inner surfaces of the absorbance cell is treated to make it hydrophilic.

6. The system of claim 5, wherein the inner surfaces of the absorbance cell are oxygen plasma treated.

7. The system of claim 5, wherein a depth of the treated material is less than the wavelength of the light emitted by the light source.

8. The system of claim 1, wherein the light source emits ultraviolet light having a wavelength less than or equal to 254 nm.

9. The system of claim 1, wherein the light detector is a spectrometer with an array detector.

10. The system of claim 1, further comprising a pump that can pump the liquid into or out of the absorbance cell.

11. A method for performing cavity-enhanced absorption spectroscopy, the method comprising:
    emitting light into a cavity-enhanced absorbance cell made of a fluorocarbon-based material that contains a liquid sample to be evaluated, the absorbance cell having diffuse reflectance inner surfaces configured to confine light and reflect the light back and forth through multiple passes such that the absorbance cell functions as an optical cavity having no mirrors;
    detecting the light after it has passed through the liquid; and
    analyzing the detected light to identify a component contained in the liquid.

12. The method of claim 11, wherein emitting light comprises emitting ultraviolet light into the absorption cell.

13. The method of claim 11, wherein the absorbance cell is made of a fluoropolymer.

14. The method of claim 11, wherein the absorbance cell is made of polytetrafluoroethylene (PTFE).

15. The method of claim 11, further comprising treating the inner surfaces of the absorbance cell to make them hydrophilic.

16. The method of claim 15, wherein treating the inner surfaces comprises oxygen plasma treating the inner surfaces of the absorbance cell.

17. The method of claim 11, wherein detecting the light comprises detecting the light with a spectrometer.

18. The method of claim 11, wherein analyzing the detected light comprises identifying the total organic carbon in the liquid and/or particles contained in the liquid.

19. The method of claim 11, wherein the component comprises particles within the liquid.

* * * * *